US008926494B1

(12) United States Patent
Cook et al.

(10) Patent No.: US 8,926,494 B1
(45) Date of Patent: Jan. 6, 2015

(54) METHOD AND APPARATUS FOR PLACEMENT OF IMPLANTABLE DEVICE ADJACENT A BODY LUMEN

(75) Inventors: Timothy C. Cook, Wayzata, MN (US); John H. Burton, Minnetonka, MN (US)

(73) Assignee: Uromedica, Inc., Plymouth, MN (US)

( * ) Notice: Subject to any disclaimer, the term of this patent is extended or adjusted under 35 U.S.C. 154(b) by 470 days.

(21) Appl. No.: 12/411,806

(22) Filed: Mar. 26, 2009

Related U.S. Application Data

(60) Provisional application No. 61/039,738, filed on Mar. 26, 2008.

(51) Int. Cl.
*A61F 2/02* (2006.01)

(52) U.S. Cl.
USPC .......................................................... 600/30

(58) Field of Classification Search
USPC .................. 600/29, 30, 31; 623/23.66, 23.77; 604/500, 502, 509
See application file for complete search history.

(56) References Cited

U.S. PATENT DOCUMENTS

| 4,832,680 | A  | * | 5/1989  | Haber et al. ........................ 600/31 |
| 5,320,617 | A  | * | 6/1994  | Leach .............................. 606/15  |
| 5,964,806 | A  |   | 10/1999 | Cook et al.                                 |
| 6,045,498 | A  | * | 4/2000  | Burton et al. ...................... 600/30  |
| 6,419,624 | B1 |   | 7/2002  | Burton et al.                               |
| 6,579,224 | B1 |   | 6/2003  | Burton et al.                               |
| 7,322,360 | B2 | * | 1/2008  | Fogarty et al. ................ 128/899     |
| 7,647,113 | B2 | * | 1/2010  | Wirbisky et al. ................ 607/41     |
| 7,744,913 | B2 | * | 6/2010  | Noyes ........................... 424/422   |
| 7,837,670 | B2 | * | 11/2010 | Barath ........................... 604/517  |
| 7,914,437 | B2 | * | 3/2011  | Gozzi et al. ...................... 600/29  |
| 2002/0010502 | A1 | * | 1/2002 | Trachtenberg .................. 607/102     |
| 2004/0230206 | A1 | * | 11/2004 | Gellman et al. ............... 606/148     |
| 2005/0228225 | A1 | * | 10/2005 | Hauschild et al. ............. 600/104     |
| 2007/0197954 | A1 | * | 8/2007  | Keenan .......................... 604/20    |

OTHER PUBLICATIONS

Gregori, Andrea, et al., "Implantation of an Adjustable Continence Therapy System Using Local Anesthesia in Patients With Post-Radical Prostatectomy", (May 1, 2008), 5 Pgs.
Gregori, Andrea, et al., "Transrectal Ultrasound Guided Implantation of the Proact Adjustable Continence Therapy System in Patients With Post-Radical Prostatectomy Stress Urinary Incontinence: A Pilot Study", The Journal of Urology, (Nov. 1, 2006), 5 pgs.
Gregori, Andrea, et al., "Transrectal Ultrasound-Guided Implantation of Adjustable Continence Therapy (Proact): Surgical Technique and Clinical Results After a Mean Follow-Up of 2 Years", (Nov. 30, 2009), 7 pgs.

* cited by examiner

*Primary Examiner* — Victoria J Hicks
*Assistant Examiner* — Raymond E Harris
(74) *Attorney, Agent, or Firm* — Schwegman Lundberg & Woessner, P.A.

(57) ABSTRACT

The present subject matter provides method and apparatus for placement of implantable devices adjacent a body lumen. A method of implanting an implantable device at a target site for controllable coaptation of a patient's urethra using an ultrasonic probe inserted into a rectum of the patient comprises inserting a Foley catheter into the urethra, expanding a Foley balloon in the bladder neck, inserting the ultrasonic probe into the rectum of the patient, using the ultrasonic probe to image the urethra and Foley balloon at the bladder neck, placing a small puncture in the perineum, passing a delivery device to the target site under ultra sonic guidance, injecting echogenic fluid at the target site adjacent the urethra, delivering the implantable device to the target site, and adjusting the implantable device to improve coaptation of the urethra.

23 Claims, 10 Drawing Sheets

METHOD AND APPARATUS FOR PLACEMENT OF IMPLANTABLE DEVICE ADJACENT A BODY LUMEN

CLAIM OF BENEFIT

This application claims the benefit under 35 U.S.C. 119(e) of U.S. Provisional Patent Application Ser. No. 61/039,738 filed on Mar. 26, 2008, which is hereby incorporated by reference in its entirety.

FIELD OF THE INVENTION

The present subject matter relates to methods and apparatus for implantable devices for treating urinary incontinence.

BACKGROUND

Implantation of medical devices into tissue of patients is complicated. Visualization methods are limited by the imaging technologies used and often do not provide an accurate picture of the physiology of the patient and the exact location of the implantable device.

There is a need in the art for improved method and apparatus for implantation of implantable devices.

SUMMARY

The present subject matter provides method and apparatus for placement of implantable devices adjacent a body lumen. Some methods include the use of ultrasound for placement of the implantable devices. Some apparatus are provided to improve imaging of the desired target site for positioning of the implantable devices. Such apparatus may be used to deliver echogenic material. Such apparatus may be used to deliver analgesic or other types of material. Such apparatus may be used for hydrodissection.

This Summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their legal equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
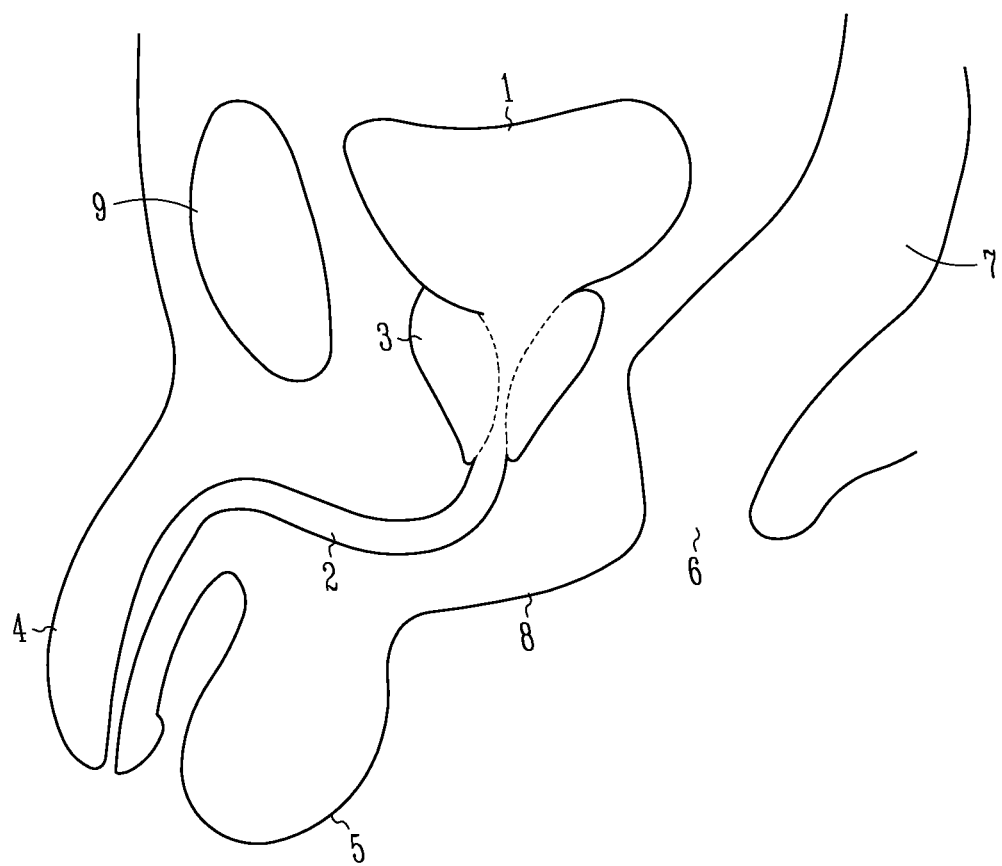
FIG. 1 is a sagittal or side view cross section showing male anatomy.

FIG. 1 is a sagittal or side view cross section showing male anatomy. The bladder 1 is connected to the urethra 2 which exits at the penis 4. A prostate gland 3 surrounds the urethra 2 near the base of the bladder 1. The urethral lumen within the prostate is shown as being constricted either by Benign Prostatic Hyperplasia (BPH) which is treated by TURP or prostate cancer which is treated by radical prostatectomy. Also shown is the scrotum 5 and perineum 8, which is the skin behind the scrotum, the anus 6 which is the opening to the rectum 7, and the pubic bone 9.

Figure 2:
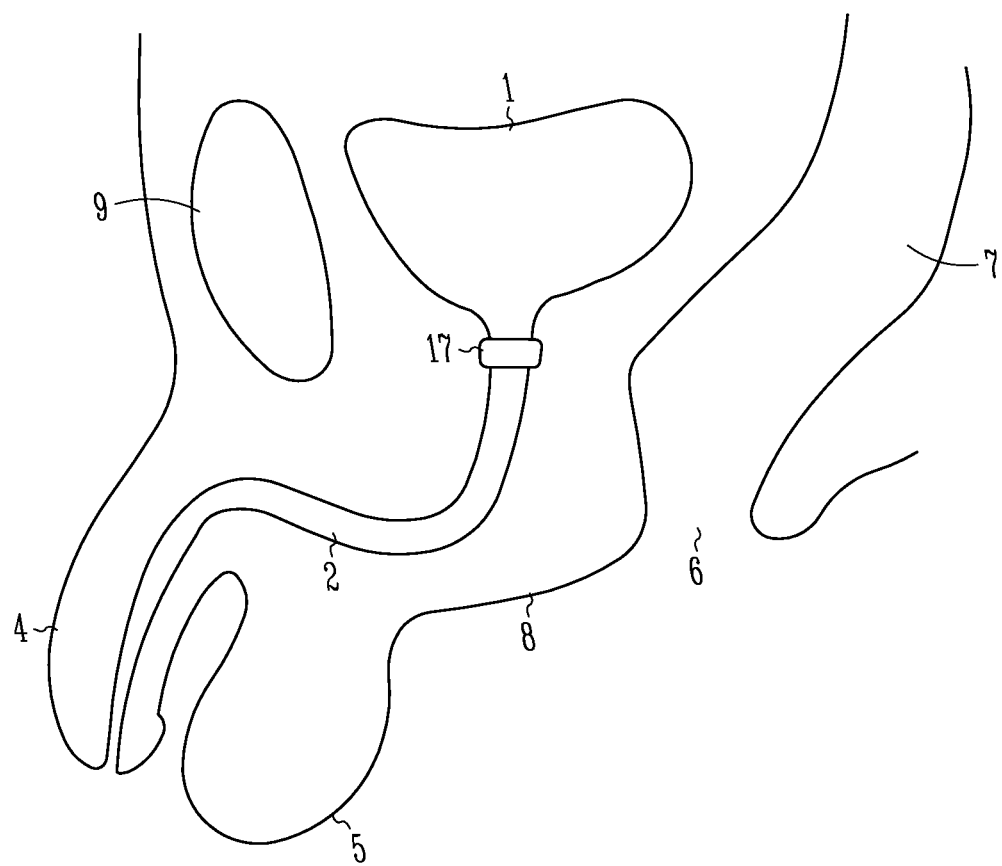
FIG. 2 is a side view cross section showing male anatomy after a radical prostatectomy.

FIG. 2 is a side view cross section showing male anatomy after a radical prostatectomy. In some embodiments, the prostate is removed during radical prostatectomy and the cut urethra is brought up and a urethral-vesical anastomosis 17 is provided to the bladder neck with sutures or staples. Removal of the prostate can damage the surrounding or adjacent tissue including the urinary sphincter and/or its enervation, resulting in incontinence due to a loss of coaptation of the urethra. One way to increase the coaptation is through the use of tissue bulking devices, such as the implantable devices described in U.S. Pat. Nos. 6,045,498, 5,964,806, 6,579,224, and 6,419,624 and their related patents and applications, the descriptions of which are hereby incorporated in their entirety.

Figure 3:
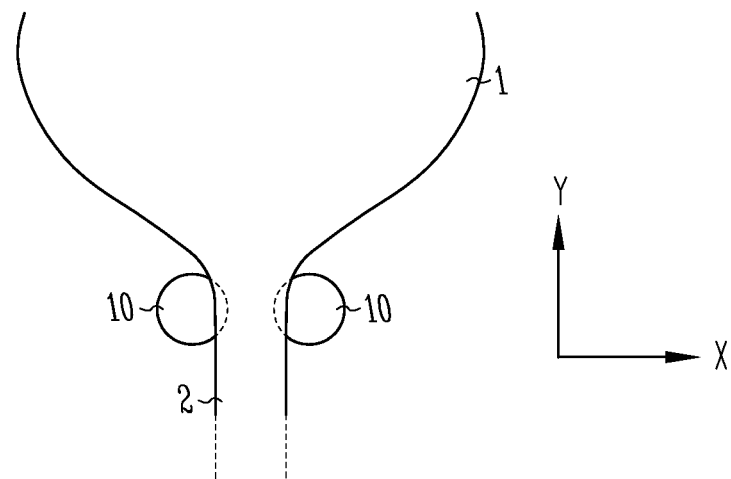
FIG. 3 is a top view showing approximate target sites of placement of implantable devices to improve coaptation of a urethra, according to one embodiment of present subject matter.

FIG. 3 is a top view of the bladder 1 and urethra 2 showing approximate target sites of placement of implantable devices 10 to improve coaptation of a urethra, according to one embodiment of present subject matter. The orientation of the y-axis is along the direction of the urethra 2 in the approximate location of implantation. The location is near the bladder neck and urethral vesical anastomosis in the case of radical prostatectomy or further down the urethra at the apex of the prostate after TURP.

Figure 4:
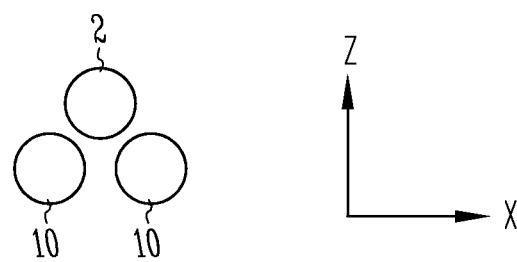
FIG. 4 is a view along the length of the urethra in the area of implantation showing approximate target sites of placement of implantable devices to improve coaptation of a urethra, according to one embodiment of present subject matter.

FIG. 4 is a view along the length of the urethra 2 in the area of implantation (or along the y-axis) showing approximate target sites of placement of implantable devices 10 to improve coaptation of a urethra, according to one embodiment of present subject matter. One of the difficulties addressed by the teachings provided herein is to assist in the proper location of the implantable devices 10. In particular, the accurate placement of the implantable devices 10 along the z-axis (sagittal view) is facilitated by the teachings of the present subject matter.

Figure 5:
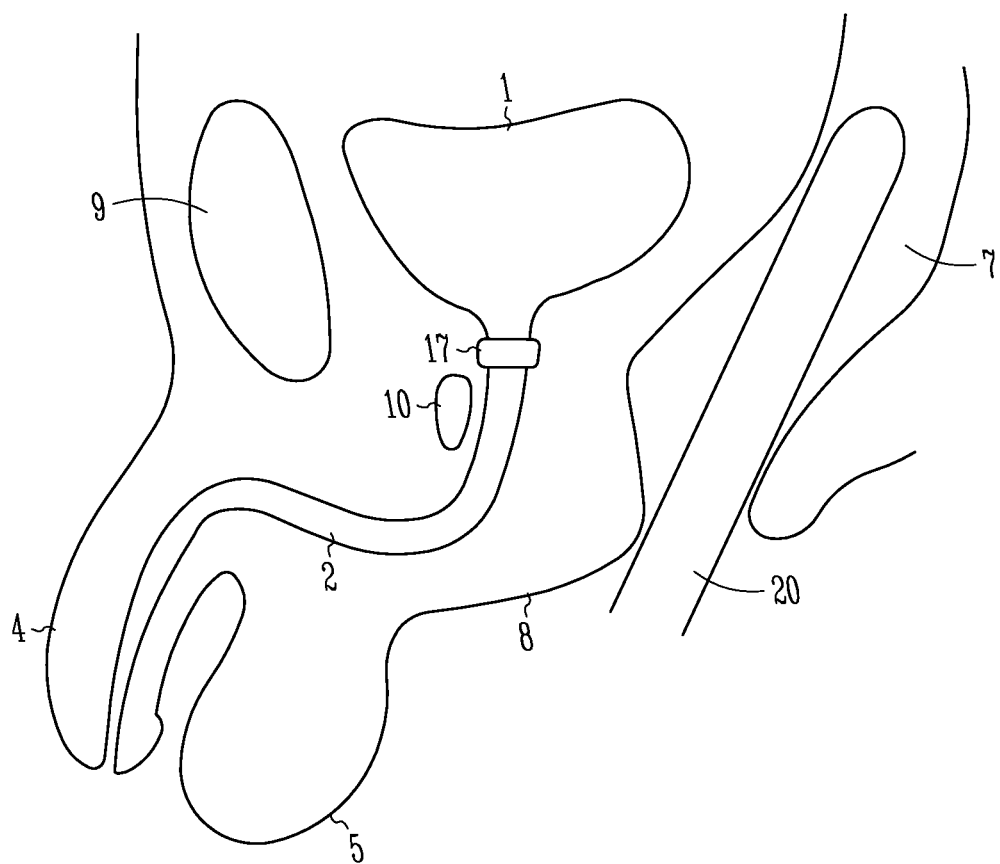
FIG. 5 is a side view cross section showing approximate placement of implantable devices in patients after radical prostatectomy, according to one embodiment of the present subject matter.

FIG. 5 is a side view cross section showing approximate placement of implantable devices 10 in patients after radical prostatectomy, according to one embodiment of the present subject matter. It is understood that implantable devices may be placed in different positions without departing from the scope of the present subject matter. Thus, it is understood that the positions shown in the figures are intended to demonstrate the present subject matter, but are not intended in an exclusive or limited sense.

One advantage of a biplanar ultrasonic rectal probe is that it can provide planar images of tissue both longitudinally in the XY plane and radially from the rectal ultrasound probe in the rectum parallel to the urethra in the XZ plane. This facilitates placement of the devices at the target site with respect to the position of the urethra and bladder.

Figure 6:
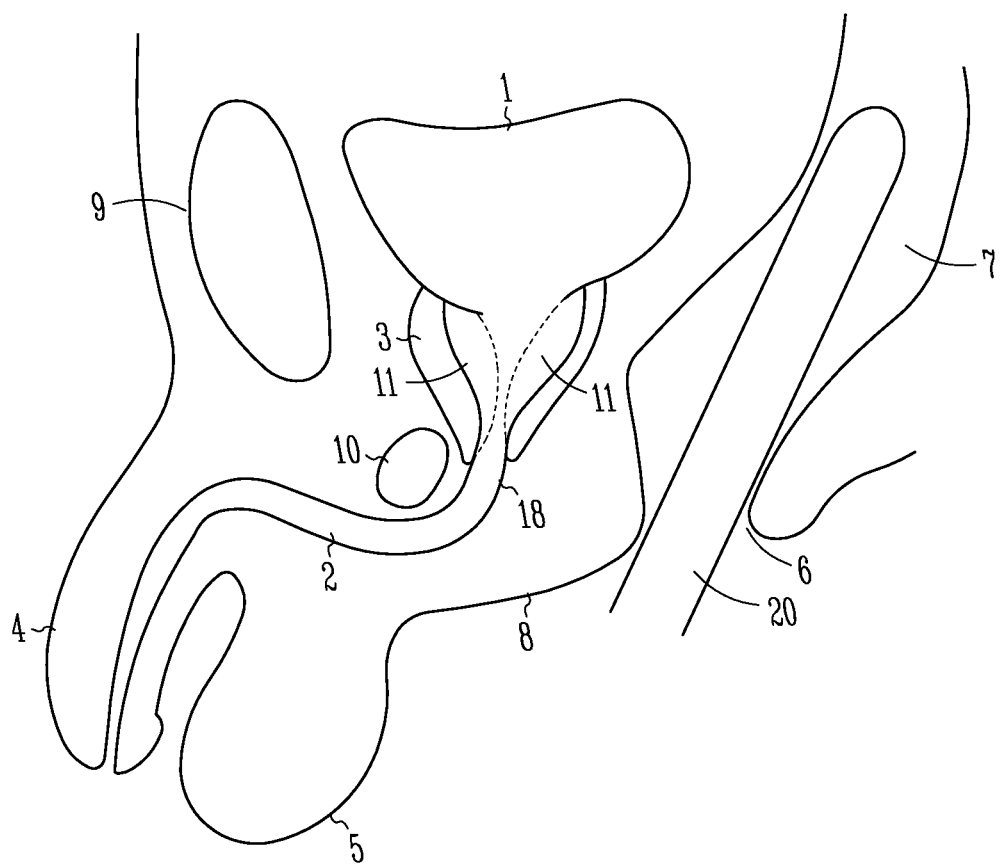
FIG. 6 is a side view cross section showing approximate placement of implantable devices after Trans-Urethral Resection of the Prostate (TURP), according to one embodiment of the present subject matter.

FIG. 6 is a side view cross section showing approximate placement of implantable devices, according to one embodiment of the present subject matter. For patients with a full or partial prostate gland 3 after TURP, the expandable portion of each implantable device 10 can be placed along the urethra near the apex of the prostate 18 to increase tissue bulking and coaptation in that area. An ultrasonic probe 20 can be inserted into the rectum 7 via the anus 6 to assist in imaging the locations of the implantable devices 10. FIG. 6 shows a prostrate gland 3 after TURP and areas 11 indicating resected portion of the prostrate.

Figure 9:
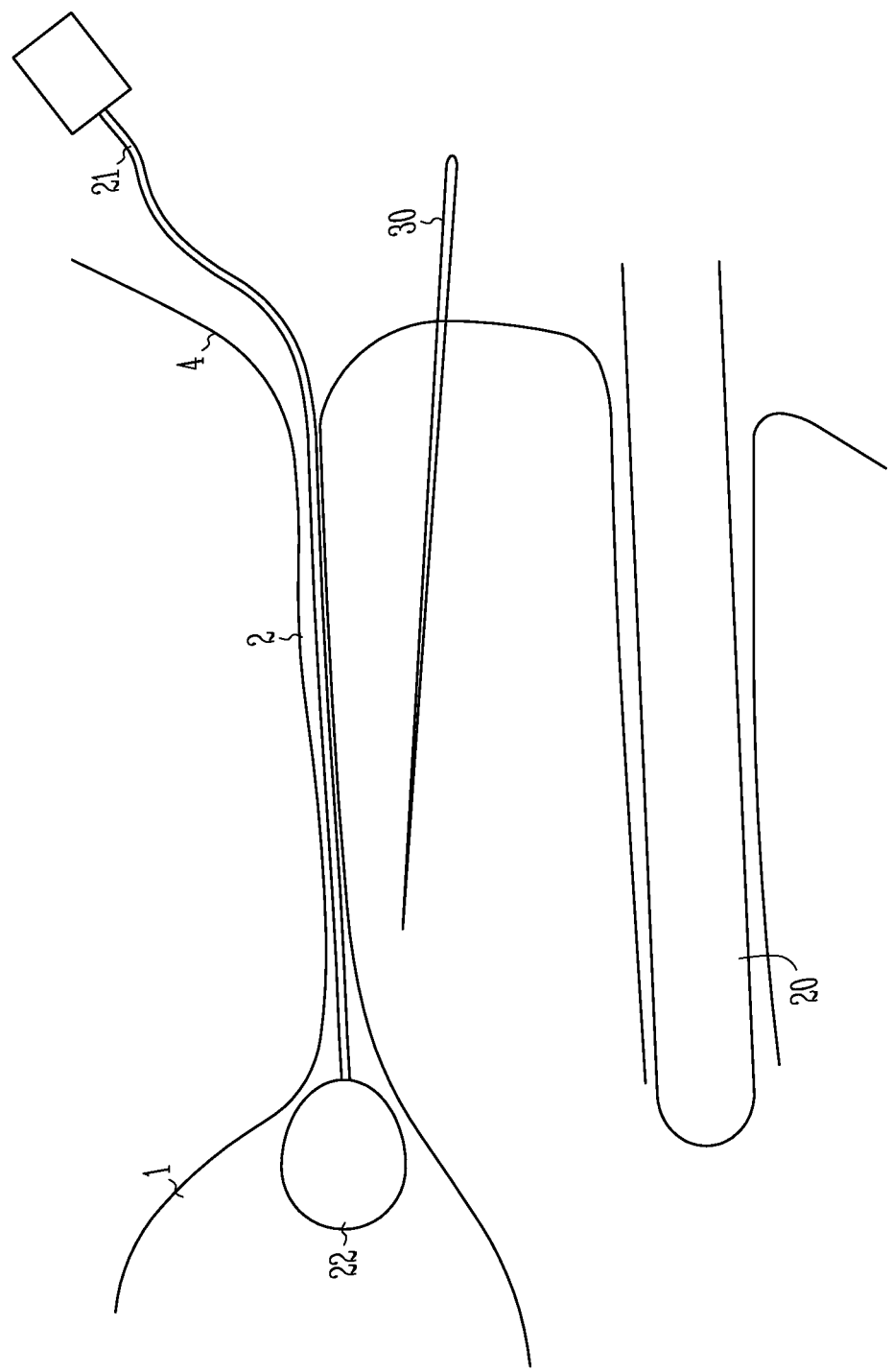
FIG. 9 shows one application of the present subject matter to a patient.

FIG. 9 shows one application of the present subject matter to a patient. An ultrasonic rectal probe 20 is used in conjunction with a Foley catheter 21 placed in the urethra with the Foley balloon 22 inflated in the bladder 1 to assist in visualizing the bladder neck and urethra 2. In such applications a doctor can rotate the rectal probe 20 to get a picture of the placement of devices with respect to the urethra in an axial segment. By rotating the probe the doctor can image the bladder neck, proximal urethra and the Foley balloon 22 sitting in the bladder neck. The doctor can also get an image of any delivery devices 30 used to deliver fluid to the target location of where the expandable portion of the implant and delivery instruments for the device itself are to be located. In various applications water can be used. Water is echogenic, so it better shows the target location of the expandable portion of the implantable device 10. In various uses the water is combined with an analgesic, such as lidocaine. In some embodiments, water with or without an analgesic can be injected at the site intended for the expandable portion of the implantable device 10 to create a pocket in the tissue so that the expandable portion will tend to stay in that position during and after inflation without migrating. This process is called "hydrodissection."

In one embodiment, the following process is employed to image the target location and accurately place the devices. It is understood that differences in method steps, order of steps, and apparatus can be made without departing from the scope of the present subject matter.

A Foley catheter is inserted into the urethra and the Foley balloon is inflated with water in the bladder neck.

An ultrasonic probe is inserted into the rectum of the patient.

The doctor uses the ultrasonic probe to image the urethra and bladder neck using the echogenetic Foley balloon as a landmark.

A small puncture in the skin in the perineum is made.

The doctor chooses a target tissue site near the bladder neck for radical prostatectomy or the apex of the prostate for TURP for placement of analgesic and fluid for hydrodissection of the targeted tissue site.

The doctor inserts a delivery device 30 into the small puncture of the perineum and, under ultrasonic visual guidance alternating between radial and longitudinal views as needed, tunnels through the tissue adjacent the urethra. As the delivery device is advanced the doctor may inject analgesic along the path, thus allowing the procedure to be done under local anesthesia.

Once at the intended delivery site more fluid can be injected to create a bolus for hydrodissection of the tissue in preparation for delivery of the expandable device.

The expandable portion of the implantable device is accurately positioned at the target site.

The implantable device is then adjusted for proper coaptation.

For devices with a septum, the septum is placed under the skin. If the procedure is done under local anesthesia the site for the septum is first anesthetized with analgesic via a needle and syringe. Such devices allow for straightforward postoperative adjustment of the urethral coaptation The other side of the urethra is then treated using the same or similar procedure.

It is understood that a doctor may manipulate the delivery device with one hand and the ultrasound with the other to get continuous imaging and feedback. The doctor can also continuously switch back and forth between a radial view and a longitudinal view to ensure that the delivery device and/or implantable device is at the right distance along the urethra or from the urethra.

Various delivery devices 30 in various embodiments can be used to introduce the echogenic fluid and place the expandable portion of the implantable devices.

Figure 10:
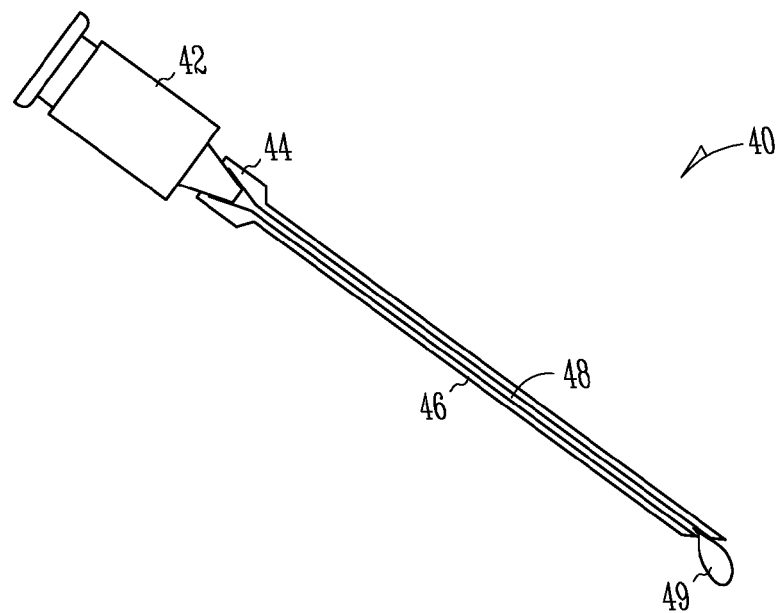
FIGS. 10-13 show some delivery devices according to various embodiments of the present subject matter.

FIG. 10 shows one embodiment of a delivery device 40. Syringe 42 is connected to Luer fitting 44 to provide fluid 49 to needle 46 via needle lumen 48. The tip of needle 46 is placed at the desired implantation target site for the expandable portion of the implantable device 10 to inject the fluid 49.

Figure 11:
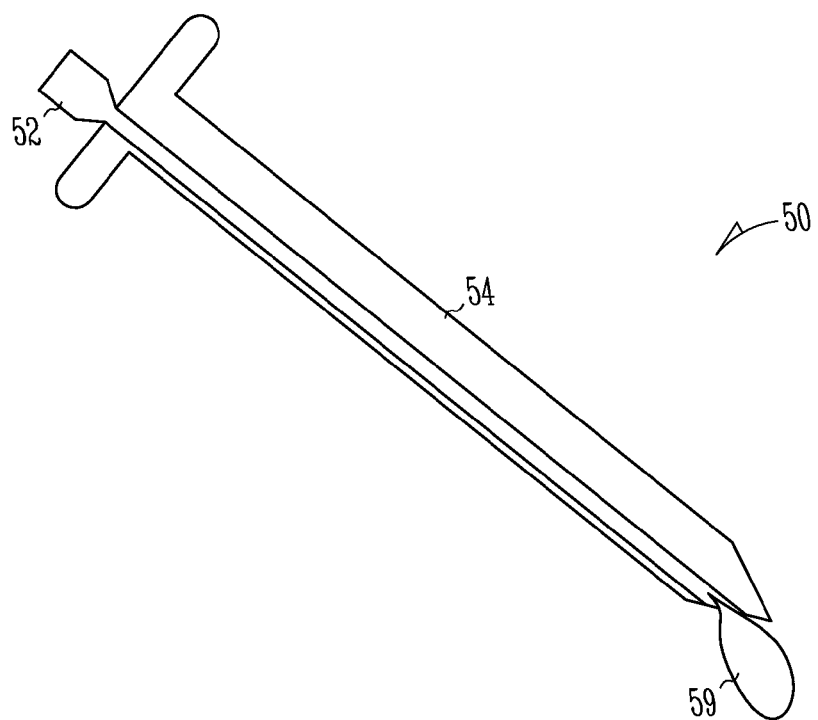

FIG. 11 shows one embodiment of a delivery device. Device 50 is a pointed trocar 54 with a removable needle portion 52 that is adapted to fit within a channel of the trocar 54. Fluid 59 may be delivered via a channel in the needle portion 52.

Figure 12:
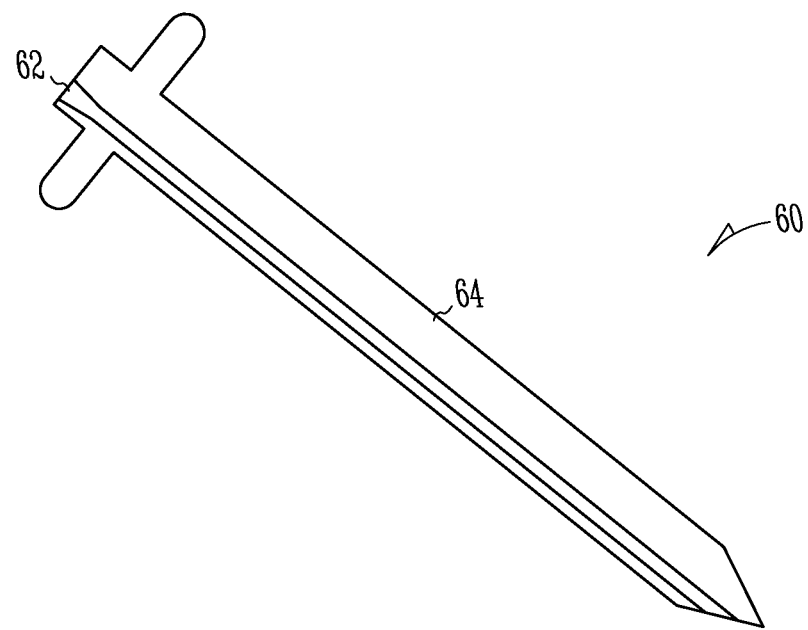

FIG. 12 shows one embodiment of a delivery device. Device 60 is a pointed trocar with fluid channel 64. Device 60 includes a Luer adaptor 62 which can facilitate transfer of fluid via the fluid channel to the implantation target site.

Figure 13:
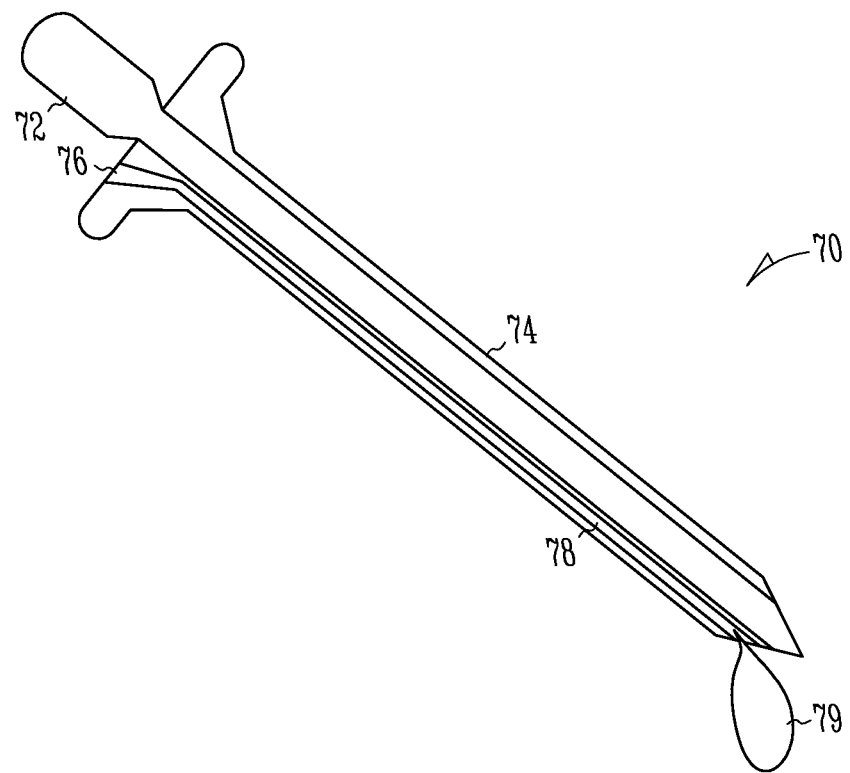

FIG. 13 shows one embodiment of a delivery device. Device 70 includes a sheath 74 that accommodates a pointed trocar 72 and includes a channel 78 with Luer adaptor 76 for delivery of fluid 79.

It is understood that a variety of different trocar, needle, and sheath combinations may be used without departing from the scope of the present subject matter. Furthermore, in various embodiments different fluid channels and Luer connections may be employed to deliver fluid to the intended target site. Additionally, delivery methods using wires placed using sheaths, trocars, and/or other assemblies may be employed to deliver implantable devices to the intended target sites. Some such delivery apparatus and methods are included in the patents and patent applications incorporated by reference herein. It is further understood that slotted trocars and/or sheaths may be employed which provide a pathway for implantable devices or needles for delivering fluid to be slid into position in various embodiments. It is also understood that certain embodiments of implantable devices may include openings or apertures that accommodate a pushrod or other wire to place the implantable devices in tissue at desired target sites. It is further contemplated that one or more implantable devices can be used to enhance coaptation and that the number of devices is not limited to those demonstrated herein. It is understood that delivery devices of various dimensions may be employed to achieve proper placement of the implantable device and septa of such devices.

In one approach the initial approach to the delivery site for the expandable element and hydrodissection at the site is made with a spinal needle. The needle is then withdrawn and replaced, again under guidance, with a device for delivering. In one embodiment, this device includes a pointed trocar within a removable sheath. Other devices and techniques are described in in the previously cited patents incorporated by reference in this application. Alternatively or in addition, in some embodiments, the trocar has a longitudinal channel through which the spinal needle can be passed with a length such that the tip of the needle is located near the tip of the trocar. Thus this trocar and needle assembly can be passed through the tissue together and the needle withdrawn after hydrodissection, obviating the need to remove the needle and replace it with a trocar. The trocar is hollow along its full length. The needle is disposed within the trocar when being inserted into the tissue. The needle is then used to deliver echogenic fluid and/or analgesic (if needed). The needle is later withdrawn from the trocar assembly to deliver the implantable device. In various embodiments, the outside diameter of the needle is closely fitted to the inside diameter of the trocar to prevent fluid from leaking back. In various embodiments, the needle has a locking hub for sealing assembly of the needle and trocar. In various embodiments, the trocar is delivered without a sheath. In various embodiments, the trocar is delivered with a sheath. In some embodiments, the sheath remains while the trocar is removed to provide a tool for delivery of the implantable device. In some embodiments a splittable sheath is used. Other embodiments are possible without departing from the scope of the present subject matter.

In one approach, a trocar with a fluid port having a Luer lock for attachment of a syringe at or near the handle and a channel along the extent of the trocar (from the port to near the trocar tip) is used. Thus obviating the need for a separate needle. In various embodiments, a Luer connection on the proximal end is provided to deliver the echogenic fluid and/or analgesic to the distal end. In various embodiments, the trocar is delivered without a sheath. In various embodiments, the trocar is delivered with a sheath. In such embodiments, the sheath remains while the trocar is removed to provide a tool for delivery of the implantable device.

In one approach, a needle is inserted and followed with a trocar. In such embodiments, the trocar acts like a dilator. In various embodiments, the trocar is delivered without a sheath. In various embodiments, the trocar is delivered with a sheath. In such embodiments, the sheath remains while the trocar is removed to provide a tool for delivery of the implantable device.

In one approach, a sheath with a channel is used to deliver the fluid and/or analgesic. In various embodiments, a sheath with a piece of thin-walled tubing of small cross sectional area provides the fluid passageway.

Better placement of the expandable portion of the implantable device provides better coaptation of the urethra with less volume. Consequently, less acute pressures on the expandable portion of the implantable device are needed. It is believed that lower volumes result in fewer device failures, fewer tissue erosion issues and less chance for device migration.

Figure 7:
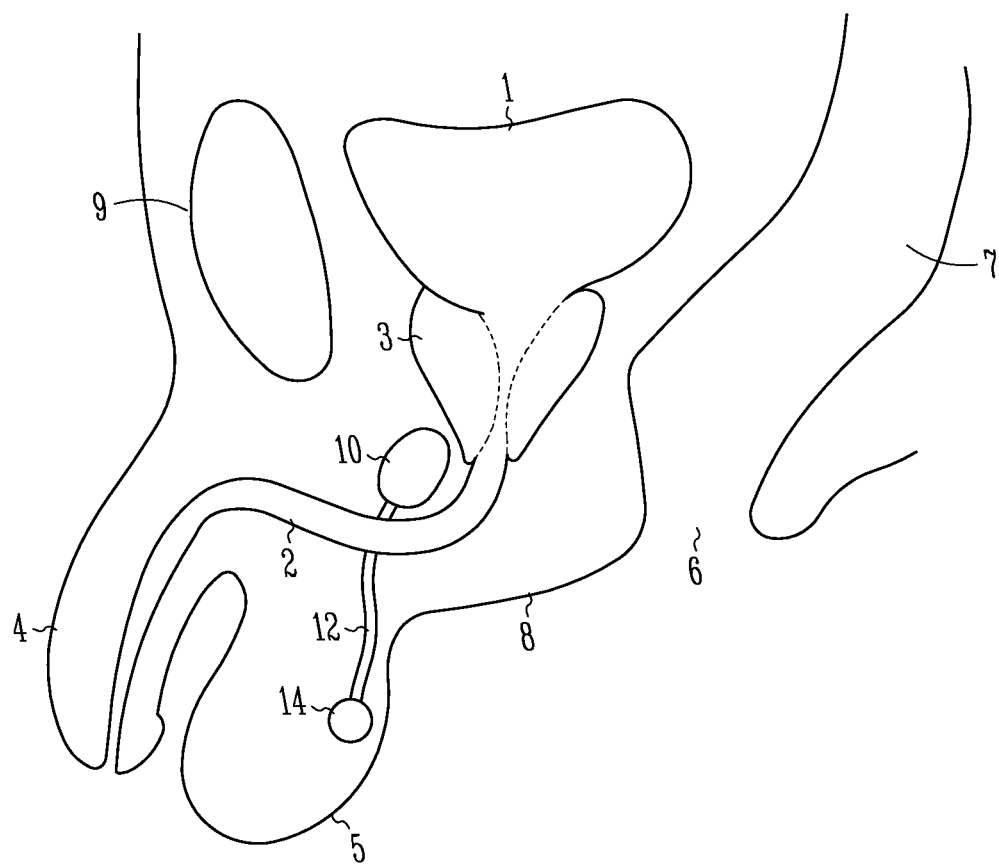
FIG. 7 is a side view cross section showing approximate placement of implantable devices including their septa after Trans-Urethral Resection of the Prostate (TURP), according to one embodiment of the present subject matter.

FIG. 7 is a side view cross section showing approximate placement of implantable devices 10 including their septa 14 and conduits 12 (in such embodiments), according to one embodiment of the present subject matter. It is understood that the septa 14 can be placed in various tissue locations, such as the scrotum 5 or somewhere in the perineal region 8. Subcutaneous placement of the septa provide for postoperative adjustment of the implantable devices by accessing the septum through the skin with a hypodermic needle. Coaptation can be adjusted by any of the procedures provided in the references incorporated by reference herein. For example, a cystoscope can be inserted into the urethra 2 to measure coaptation. Other devices, placements, and approaches are possible without departing from the present subject matter.

Figure 8:
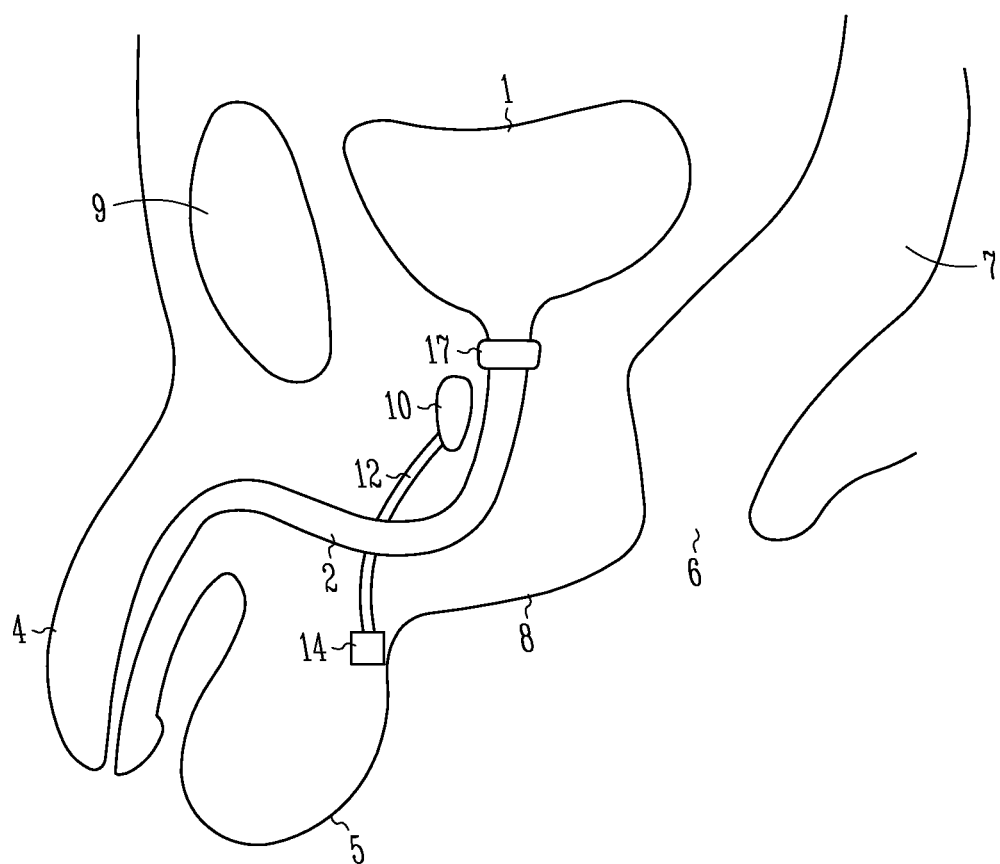
FIG. 8 is a side view cross section showing approximate placement of implantable devices including their septa after radical prostatectomy, according to one embodiment of the present subject matter.

FIG. 8 is a side view cross section showing approximate placement of implantable devices 10 including their septa 14 and conduits 12 (in such embodiments), according to one embodiment of the present subject matter. It is understood that the septa 14 can be placed in various tissue locations, such as the scrotum 5 or somewhere in the perineal region 8. Subcutaneous placement of the septa provide for postoperative adjustment of the implantable devices. Coaptation can be adjusted by any of the procedures provided in the references incorporated by reference herein. For example, a cystoscope can be inserted into the urethra 2 to measure coaptation. Other devices, placements, and approaches are possible without departing from the present subject matter.

While the method and apparatus provided herein are demonstrated for application to the male, it is understood that they are applicable to female applications as well. Likewise they are applicable in general to provide coaptation to other lumens within the body such as the anal canal and rectum or the esophagus.

It is understood that various implantable devices may be employed. The imaging of such devices may be enhanced by adding echogenic coating or elements within the expandable portion. Various imaging methods may include temporarily filling the expandable portion with air to provide enhanced visibility via ultrasound. Other approaches are possible without departing from the scope of the present subject matter.

This application is intended to cover adaptations and variations of the present subject matter. It is to be understood that the above description is intended to be illustrative, and not restrictive. The scope of the present subject matter should be determined with reference to the appended claim, along with the full scope of legal equivalents to which the claims are entitled.

What is claimed is:

1. A method of positioning and implanting an expandable implantable device at a target site for controllable coaptation of a male patient's urethra using a biplanar ultrasonic probe inserted into a rectum of the patient, comprising:
    inserting a Foley catheter into the urethra;
    expanding a Foley balloon in the bladder neck;
    inserting the ultrasonic probe into the rectum of the patient;
    using the ultrasonic probe to image the urethra and Foley balloon at the bladder neck;
    placing a small puncture in the perineum;
    passing a delivery device through the puncture to the target site with concurrent delivery of a local anesthetic under guidance of the ultrasonic probe and positioning the delivery device at the target site, using radial and longitudinal views provided by the ultrasonic probe, wherein the target site is proximal to the apex of the prostate or an urethral vesical anastomosis;

expanding the target site using fluid delivered from the delivery device;

delivering the expandable implantable device to the expanded target site; and adjusting the expandable implantable device to improve coaptation of the urethra, wherein the amount of the expansion of the expandable implantable device controls the coaptation of the urethra.

2. The method of claim 1, wherein passing a delivery device includes passing a pointed trocar to the target site under ultrasonic guidance.

3. The method of claim 2, further comprising passing a needle through the trocar.

4. The method of claim 3, further comprising injecting echogenic fluid through a channel of the needle to hydrodissect the target area.

5. The method of claim 4, wherein delivering the expandable implantable device includes removing the needle from the trocar.

6. The method of claim 2, wherein passing a pointed trocar includes coupling a syringe to a Luer coupling of the trocar.

7. The method of claim 2, further comprising injecting echogenic fluid through a channel of the trocar to hydrodissect the target area.

8. The method of claim 2, wherein delivering the expandable implantable device includes delivering the expandable implantable device through a channel of the trocar.

9. The method of claim 1, wherein passing a delivery device includes passing a pointed trocar enclosed within a channel of a removable sheath to the target site under ultrasonic guidance.

10. The method of claim 9, further comprising injecting echogenic fluid through a channel of the trocar to hydrodissect the target area.

11. The method of claim 9, further comprising injecting echogenic fluid through a second channel of the sheath to hydrodissect the target area.

12. The method of claim 9, wherein delivering the expandable implantable device includes delivering the expandable implantable device through a channel of the trocar to the target site.

13. The method of claim 9, wherein delivering the expandable implantable device includes removing the trocar from the channel of the sheath before delivering the expandable implantable device to the target site.

14. The method of claim 1, wherein the fluid is an echogenic fluid delivered at the target site adjacent the urethra.

15. The method of claim 14, wherein the echogenic fluid includes water and is delivered via injection.

16. The method of claim 14, wherein injecting includes hydrodissecting the target site with the fluid to create a pocket for the expandable implantable device.

17. The method of claim 1, wherein placing a small puncture includes placing a small puncture in the perineum using a spinal needle.

18. The method of claim 17, further comprising passing the spinal needle through to the target site.

19. The method of claim 1, wherein the local anesthetic is delivered via injection in an echogenic fluid.

20. The method of claim 1, wherein passing a delivery device includes passing a splittable sheath enclosing a trocar to the target site under ultrasonic guidance.

21. The method of claim 1, wherein adjusting the expandable implantable device includes accessing a septum connected to the expandable implantable device with a hypodermic needle to improve coaptation of the urethra.

22. The method of claim 1 wherein the patient has had a transurethral resection of the prostate or a radical prostatectomy.

23. A method of positioning and implanting an expandable implantable device at a target site for controllable coaptation of a patient's urethra using a biplanar ultrasonic probe inserted into a rectum of the patient, comprising:

providing a patient having a Foley catheter in the urethra with a Foley balloon expanded in the bladder neck, a biplanar ultrasonic probe in the rectum, and a puncture in the perineum;

passing a delivery device through the puncture in the perineum of the patient towards a target site and positioning the delivery device at the target site, under guidance of the ultrasonic probe using radial and longitudinal views provided by the ultrasonic probe, wherein the delivery device delivers an echogenic fluid having a local anesthesic along the passage;

expanding the target site using hydrodissection;

delivering the expandable implantable device to the expanded target site; and adjusting the expandable implantable device to improve coaptation of the urethra, wherein the amount of the expansion of the expandable implantable device controls the coaptation of the urethra.

* * * * *